(12) United States Patent
Yano et al.

(10) Patent No.: US 8,640,326 B2
(45) Date of Patent: Feb. 4, 2014

(54) ELECTRIC WIRE TESTING APPARATUS AND ELECTRIC WIRE PROCESSOR EQUIPPED THEREWITH

(75) Inventors: Tetsuya Yano, Hyogo (JP); Etsuro Nishida, Hyogo (JP)

(73) Assignee: Shinmaywa Industries, Ltd., Hyogo (JP)

( * ) Notice: Subject to any disclaimer, the term of this patent is extended or adjusted under 35 U.S.C. 154(b) by 240 days.

(21) Appl. No.: 13/109,198

(22) Filed: May 17, 2011

(65) Prior Publication Data

US 2012/0047724 A1 Mar. 1, 2012

(30) Foreign Application Priority Data

Sep. 1, 2010 (JP) ................................. 2010-195382

(51) Int. Cl.
*H01R 43/28* (2006.01)
*G01N 21/952* (2006.01)

(52) U.S. Cl.
USPC .............................. 29/705; 29/593; 356/242.1

(58) Field of Classification Search
CPC ............................... H01R 43/28; G01N 21/952
USPC .......... 29/593, 729, 748, 753, 705; 356/242.1
See application file for complete search history.

(56) References Cited

U.S. PATENT DOCUMENTS

| 5,293,220 A | 3/1994 | Fukuda et al. |
| 5,619,792 A | 4/1997 | Ohmori et al. |
| 5,691,763 A | 11/1997 | Ichikawa et al. |

FOREIGN PATENT DOCUMENTS

| JP | 05-079824 A | | 3/1993 |
| JP | 2004-156910 A | | 6/2004 |
| JP | 2007135286 A | * | 5/2007 |
| JP | 2008-180579 A | | 8/2008 |

* cited by examiner

*Primary Examiner* — Livius R Cazan
(74) *Attorney, Agent, or Firm* — Keating & Bennett, LLP (57) ABSTRACT

An electric wire testing apparatus tests the condition of an end portion of an electric wire including a plurality of core wires and a sheath for covering the core wires. The electric wire testing apparatus includes an imaging device arranged to photograph an end surface of the core wires that have been exposed by stripping off the sheath, a counting unit arranged to count the number of the core wires from an image photographed by the imaging device, and a determining unit arranged to determine pass/fail of the condition of the end portion of the electric wire based on whether or not the number of the core wires counted by the counting unit matches a predetermined number.

7 Claims, 9 Drawing Sheets

ELECTRIC WIRE TESTING APPARATUS AND ELECTRIC WIRE PROCESSOR EQUIPPED THEREWITH

BACKGROUND OF THE INVENTION

1. Field of the Invention

The present invention relates to an electric wire testing apparatus for testing the condition of an end portion of an electric wire that includes a plurality of core wires and a sheath for covering the core wires. The present invention also relates to an electric wire processor equipped with the testing apparatus.

2. Description of the Related Art

As a conventional example of this type of testing apparatus, the testing apparatus disclosed in JP 05-079824A has been known. This testing apparatus has a lighting means for illuminating an end of the core wires from which the sheath has been stripped off, an imaging means disposed facing the lighting means, for photographing the end portion of the core wires from the side, and an image processing means for processing an image photographed by the imaging means, and a monitor for displaying an image processed by the image processing means. This testing apparatus tests the condition of an end portion of an electric wire based on, for example, the coordinate positions of the sheath and the core wires and the inclinations of the core wires, which are obtained from the brightness data of the photographed image.

However, the testing apparatus uses only the images of the core wires photographed from one side. Therefore, a problem with this testing apparatus is that if the other side of the core wires has a defect, the defect cannot be detected. For example, if some of the core wires are damaged and lost or some of the core wires are untied in the side that is not photographed, the testing apparatus cannot detect such defects.

JP 2004-156910A discloses an apparatus that photographs the end faces of the core wires with an imaging means and tests the end portion of the core wires for pass/fail based on the total sum of the areas of the end faces in the photographed image.

However, the apparatus that tests a wire end for pass/fail based on the total sum of the areas of the end faces of the core wires may falsely determine a defective product as a non-detective product although some of the core wires are missing, when the total sum of the areas may happen to satisfy a predetermined condition.

Moreover, it is not always easy to measure the areas of the end faces of the core wires accurately. For example, when the sheath of the electric wire which is stripped off is relatively long, the end faces of the core wires that are adjacent to each other have a wide gap therebetween. However, when the gap between the end faces of the core wires is wide, it becomes difficult to measure the areas of the end faces of the core wires accurately. Thus, the apparatus that tests a wire end for pass/fail based on the total sum of the areas of the end faces of the core wires has the problem of low test accuracy for an electric wire having core wires that tend to be untied easily.

SUMMARY OF THE INVENTION

Preferred embodiments of the present invention provide an electric wire testing apparatus that accurately tests a condition of an end portion of an electric wire, and provide an electric wire processor that includes such an electric wire testing apparatus.

According to a preferred embodiment of the present invention, an electric wire testing apparatus for testing a condition of an end portion of an electric wire including a plurality of core wires and a sheath to cover the core wires, includes an imaging device arranged to photograph an end surface of the core wires that have been exposed by stripping off the sheath; a counting unit arranged to count a number of the core wires based on an image photographed by the imaging device; and a determining unit arranged to determine a pass/fail of the condition of the end portion of the electric wire based on whether or not the number of the core wires counted by the counting unit matches a predetermined number.

Another preferred embodiment of the present invention also provides an electric wire processor including the above-described electric wire testing apparatus. The electric wire processor also preferably includes a conveying unit arranged to hold and convey the electric wire; a cutter unit arranged to cut the electric wire and strip off the sheath; and a terminal crimping unit arranged to crimp a terminal onto an end portion of the electric wire from which the sheath has been stripped off. The electric wire testing apparatus is configured to test the condition of the end portion of the electric wire while the conveying unit is conveying the electric wire from the cutter unit to the terminal crimping unit.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

First Preferred Embodiment

Figure 1:
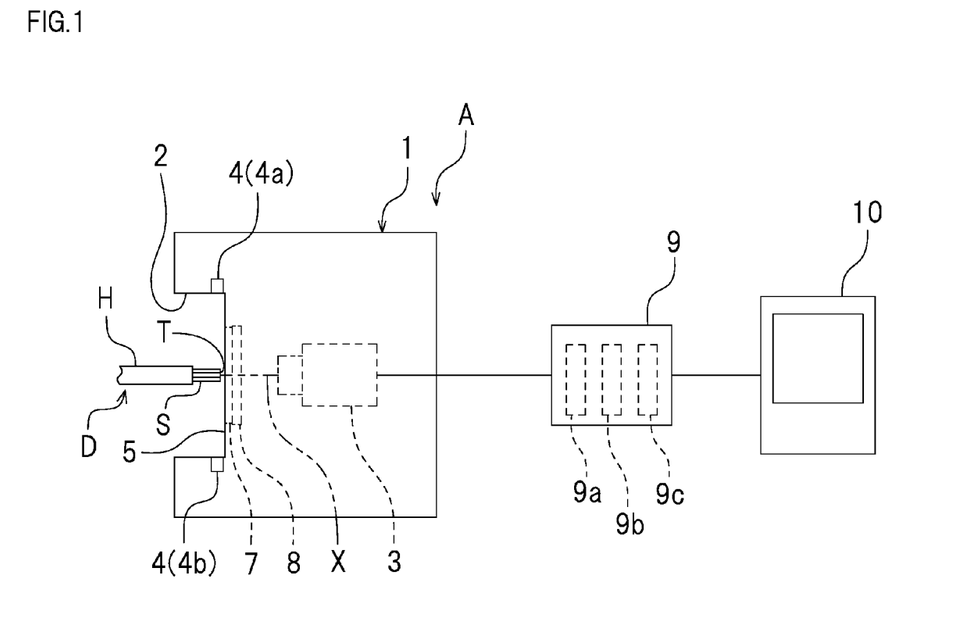
FIG. 1 is a configuration diagram illustrating an electric wire testing apparatus.

Hereinbelow, a first preferred embodiment of an electric wire testing apparatus (hereinafter referred to simply as "the testing apparatus") according to the present invention will be described. The testing apparatus A shown in FIG. 1 preferably includes an apparatus main unit 1, a CCD camera 3 (hereinafter referred to simply as "the camera 3") as one example of the imaging device, a photosensor 4, a computer 9, and a display device 10. The testing apparatus A tests the condition of an end portion of an electric wire D. The type of the test subject, i.e., the electric wire D, is not particularly limited. The electric wire D includes, for example, a plurality of core wires S made of metal, and a sheath H made of a synthetic resin, which covers the core wires S.

Figure 2:
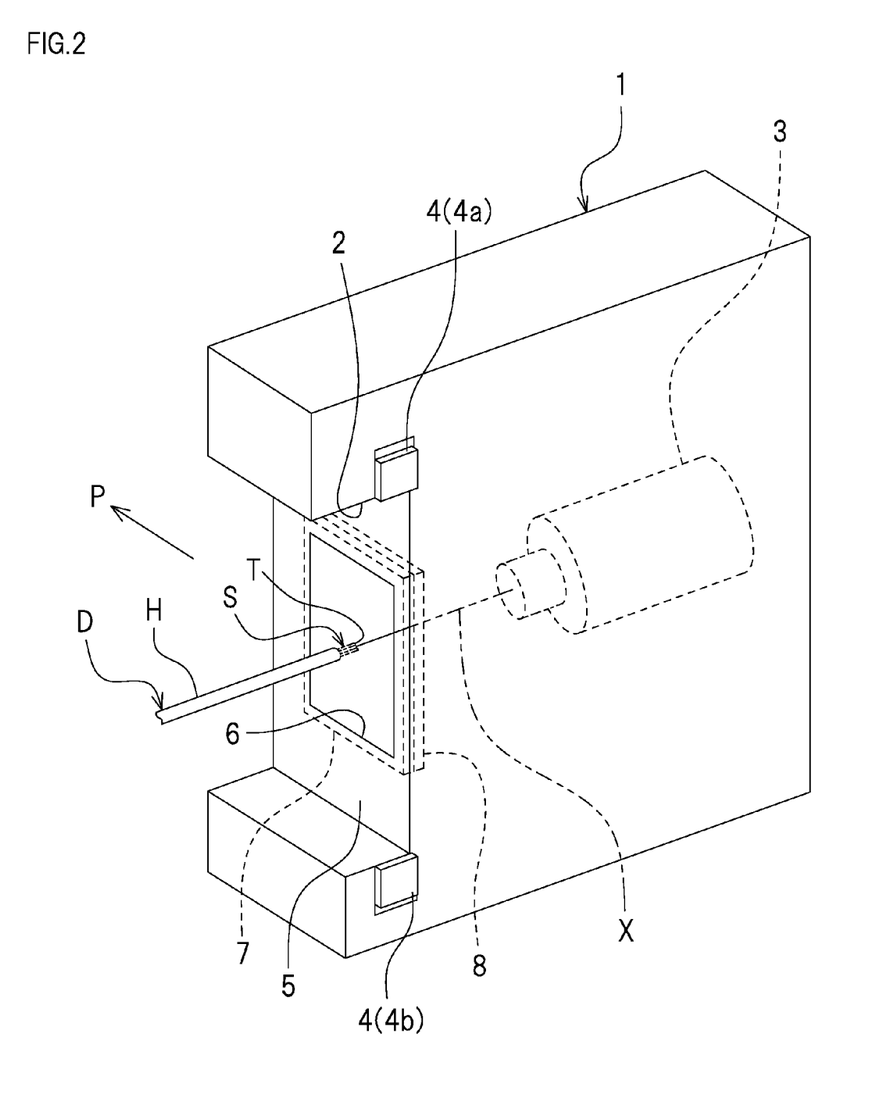
FIG. 2 is a perspective view of the apparatus main unit of the electric wire testing apparatus.

As illustrated in FIG. 2, the apparatus main unit 1 preferably has a vertically long box shape. The camera 3 is accommodated in the apparatus main unit 1. The apparatus main unit 1 includes a recessed portion 2 that is recessed toward the rear. An opening 6 is formed in a front surface 5 of the apparatus main unit 1. The opening 6 preferably has a rectangular shape, for example. It should be noted, however, that the opening 6 may have any shape. The opening 6 is located in front of the camera 3. The opening 6 is closed by a transparent glass plate 7. A lighting unit 8, disposed around the imaging axis X of the camera 3, is provided inside the glass plate 7. The lighting unit 8 includes a plurality of LEDs arrayed in a substantially ring shape. It should be noted, however, that the lighting unit 8 is not limited to LEDs but may be other types of light sources.

The photosensor 4 is one example of a sensor arranged to sense that an end portion of the electric wire D is located in front of the apparatus main unit 1. The photosensor 4 senses the electric wire D that is conveyed in the recessed portion 2 in the direction indicated by the arrow P in FIG. 2. The photosensor 4 includes an illuminating unit 4a and a light receiving unit 4b. The illuminating unit 4a is disposed above the front surface 5 and is configured to emit light downward. The light receiving unit 4b is disposed below the front surface 5. It should be noted, however, that the illuminating unit 4a may be disposed below the front surface and the light receiving unit 4b may be disposed above the front surface 5. When the electric wire D passes between the illuminating unit 4a and the light receiving unit 4b, the electric wire D blocks the light emitted from the illuminating unit 4a. Thereby, the photosensor 4 can sense that the electric wire D is present in front of the front surface 5. Upon sensing the electric wire D, the photosensor 4 transmits a sensing signal. The camera 3 and the lighting unit 8 are actuated based on the sensing signal from the photosensor 4. When the electric wire D passes through a region of the imaging axis X of the camera 3, the lighting unit 8 emits light and the camera 3 takes an image. At this time, the end surface T of the core wires S of the electric wire D is photographed.

The computer 9 preferably includes, for example, a CPU, a ROM, and a RAM, which are not shown in the drawings. The CPU executes a predetermined process according to a program stored in, for example, the ROM. At this time, the computer 9 functions as a counting unit 9a to count the number of the core wires S of the electric wire D. The computer 9 also functions as a determining unit 9b to determine pass/fail of the condition of an end portion of the electric wire D. The computer 9 counts the number of the core wires S from the photographed image of the end surface T of the core wires S, and determines pass/fail of the condition of the end portion of the electric wire D based on the result of the counting. How the number of the core wires S is counted and how pass/fail of the electric wire D is determined will be described later. The testing apparatus A can test a plurality of types of electric wires D. The ROM stores data for a plurality of types of electric wires that can be the test subjects. The ROM is one example of a storage device 9c. In place of the ROM internal of the computer 9, it is also possible to use an external storage device (such as a hard disk, an optical disk, and a USB memory) as the storage device 9c. The computer 9 may be either a dedicated computer designed for the testing apparatus A or a general-purpose computer such as a personal computer. The type of the computer 9 is not particularly limited.

Figure 3:
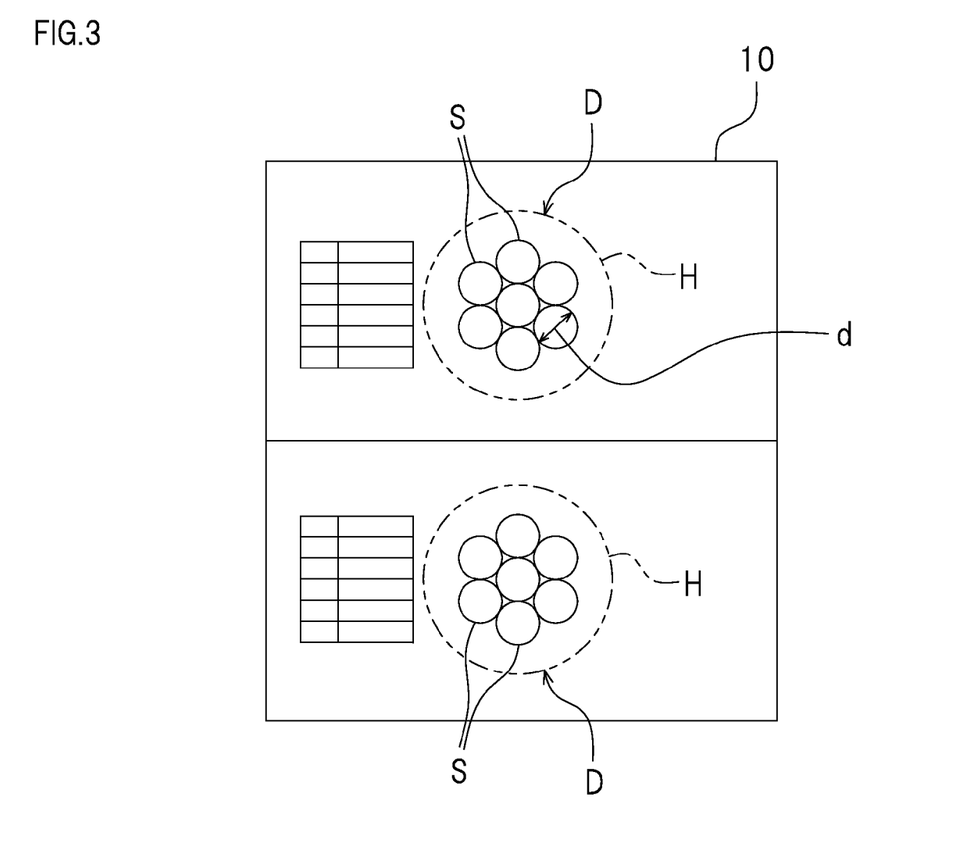
FIG. 3 is a view illustrating one example of images displayed on the display device.

The display device 10 may be of any type as long as it is capable of displaying images photographed by the camera 3. For example, a liquid crystal display can be suitably used as the display device 10. The photographed images by the camera 3 and the determination results of the condition of the electric wire D, for example, are displayed on the display device 10, as illustrated in FIG. 3.

Figure 4:
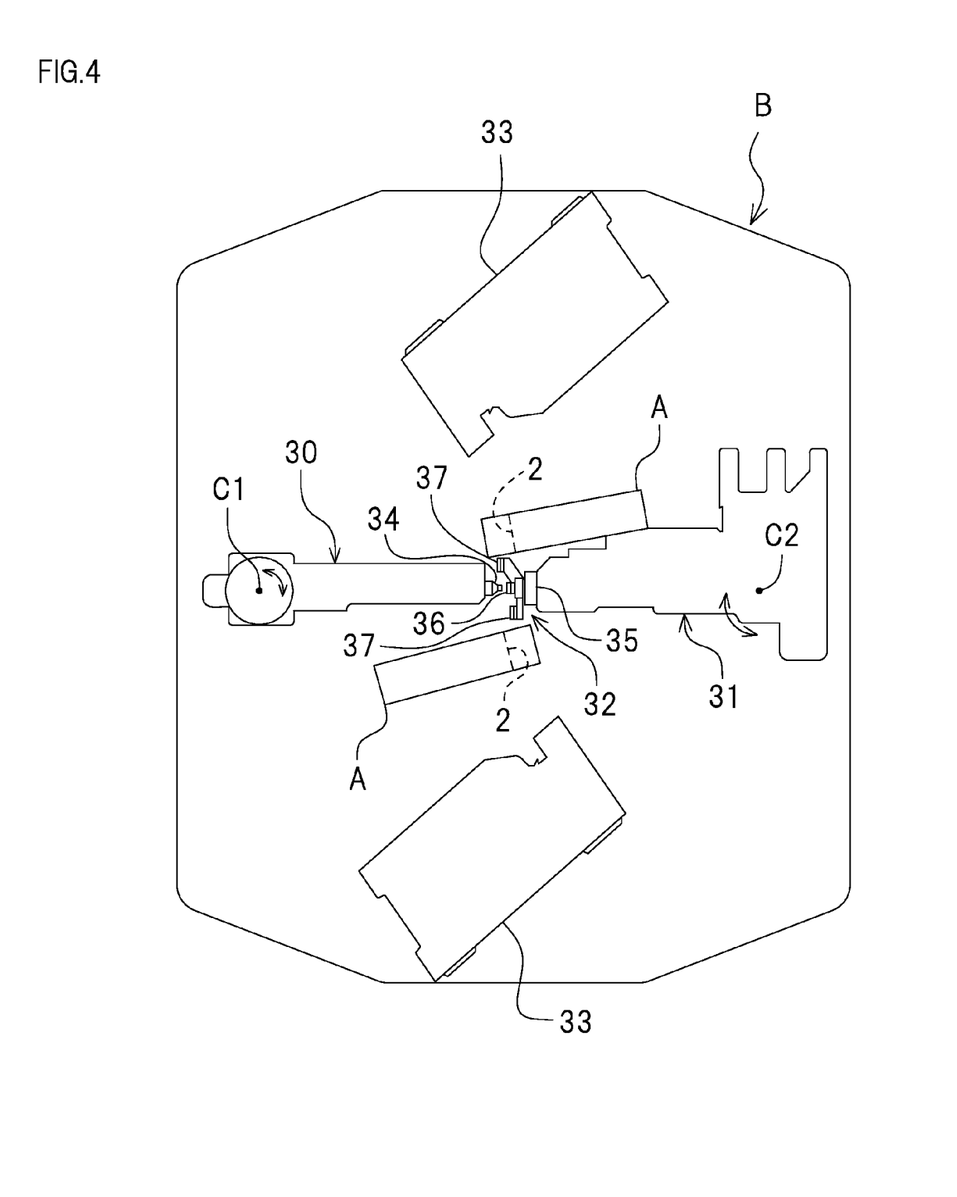
FIG. 4 is a plan view schematically illustrating the configuration of an electric wire processor.

The testing apparatus A can be used, for example, as a portion of an electric wire processor B as illustrated in FIG. 4. The electric wire processor B preferably includes a front conveying unit 30 and a rear conveying unit 31, a cutter unit 32 arranged between the foremost ends of the two conveying units 30 and 31, and front and rear crimping unit 33 to crimp a terminal onto the core wires S of the electric wire D. The testing apparatuses A are provided at respective sides of the conveying units 30 and 31. The testing apparatuses A are disposed between the cutter unit 32 and the crimping units 33.

Clamp mechanisms 34 and 35 capable of holding the electric wire D are provided respectively at the foremost ends of the conveying units 30 and 31. The electric wire D, which is transferred from the left to the right of FIG. 4 in the front conveying unit 30, is passed through the clamp mechanism 34 and is supplied to the clamp mechanism 35 of the rear conveying unit 31. The conveying units 30 and 31 can turnaround the centers C1 and C2, respectively, near the base end portions. The conveying units 30 and 31 are driven by motors, not shown in the drawings. The cutter unit 32 includes a cutting blade 36 arranged to cut the electric wire D, and front and rear stripping blades 37 provided at opposite sides of the cutting blade 36.

Next, the operations of the electric wire processor B will be described. First, the electric wire D is transferred from the front conveying unit 30 to the rear conveying unit 31, and is held by the clamp mechanisms 34 and 35. The electric wire D is cut into two pieces by the cutting blade 36 of the cutter unit 32. Next, the conveying units 30 and 31 turn around the centers C1 and C2, so that the respective pieces of the electric wire D are positioned in front of the stripping blades 37. The stripping blades 37 cut into the sheaths H of the pieces of the electric wire D, and thereafter, the pieces of the electric wire D are pulled toward opposite sides of the stripping blades 37. The sheath H of each piece of the electric wire D is stripped off.

Thereafter, the conveying units 30 and 31 further turn until the end portions of the electric wire D respectively move to the front surfaces of the crimping units 33. During this time, the end portions of the electric wire D cross the recessed portions 2 of the respective testing apparatuses A (see FIG. 2). The end portions of the electric wire D are tested by the testing apparatuses A. The electric wire processor B includes the frontward and rearward testing apparatuses A. The frontward end portion and the rearward end portion of the electric wire D are tested almost simultaneously. For this reason, the testing time can be shortened. The processing by the electric wire processor B can be made quicker. If the testing apparatuses A determine the electric wire D as a non-detective product, the conveying units 30 and 31 further turn so that the pieces of the electric wire D are conveyed to the crimping units 33. A terminal is crimped onto the end portion of each piece of the electric wire D. On the other hand, if at least one of the testing apparatuses A determines that the electric wire D is defective, a predetermined process is performed. For example, a message to that effect is displayed on the display device 10, and the condition of the end portion of the electric wire D is checked again by the operator. Alternatively, a process in which the conveying units 30 and 31 eject the defective product from the apparatus, for example, is performed.

Next, the test performed by the testing apparatus A will be described. As already described above, when the electric wire D passes the front surface 5 of the apparatus main unit 1, the photosensor 4 senses the electric wire D. When the electric wire D is sensed, the lighting unit 8 emits light and the camera 3 photographs the end surface T of the core wires S of the electric wire D. The photographed image is displayed on the display device 10. Here, as illustrated in FIG. 3, the end surface of the core wires S of the frontward piece of the electric wire D is displayed in the upper portion, and the end surface of the core wires S of the rearward piece of the electric wire D is displayed in the lower part. Both end surfaces of the core wires S of the frontward and rearward pieces of the electric wire are displayed simultaneously on the display device 10. It should be noted, however, that the method of displaying the end surface of the core wires S of the electric wire D on the display device 10 is not particularly limited.

The computer 9 counts the number of the core wires S from the photographed image, and determines pass/fail of the condition of the end portion the electric wire D based on the number of the core wires S. Next, the method for counting the number of the core wires S and the method for determining pass/fail of the electric wire D will be described with reference to the flow-chart of FIG. 5. The following processes are executed by the CPU of the computer 9.

Figure 5:
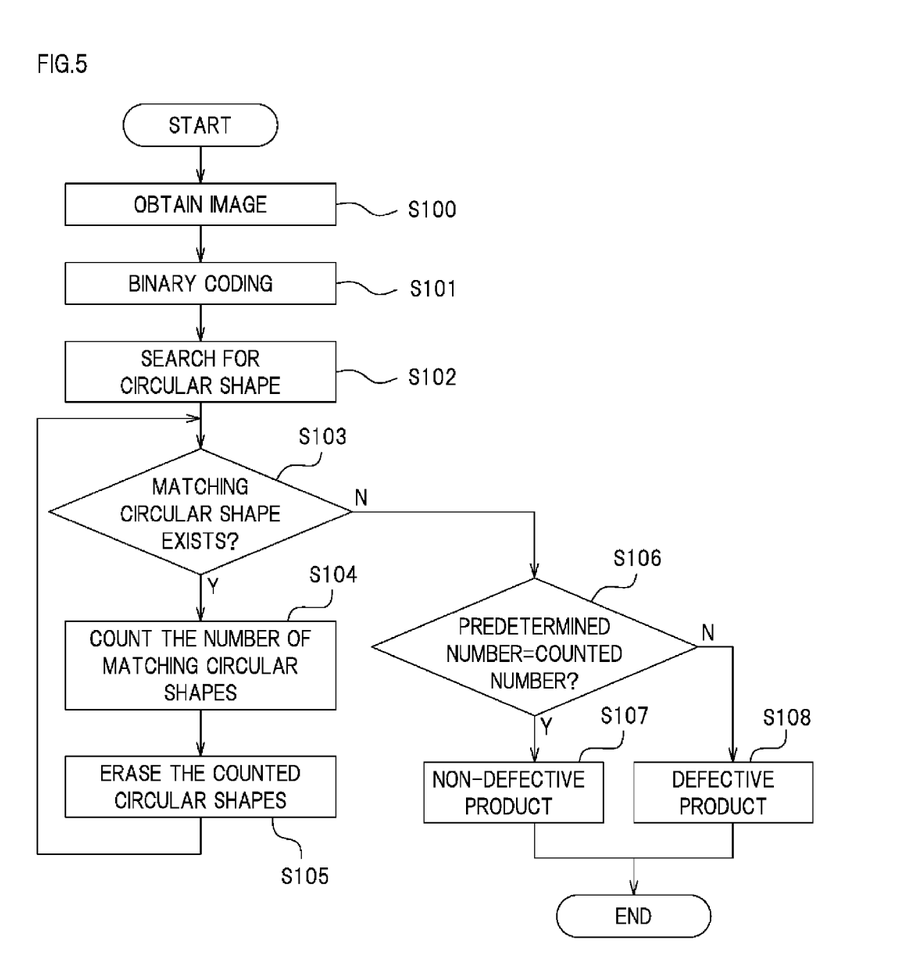
FIG. 5 is a flow-chart for illustrating a testing method according to a first preferred embodiment of the present invention.

As illustrated in FIG. 5, first, data of the photographed image are acquired at step S100. At step S101, binary coding is performed for the photographed image based on a preset threshold value. That is, the brightness of each pixel of the photographed image is compared with the just-mentioned threshold value, and the pixels having higher brightness than the threshold value are defined as bright portions whereas the pixels having lower brightness than the threshold value are defined as dark portions. Thus, an image containing bright portions and dark portions is obtained. In this process, what is called edge enhancement may be performed in order to make the boundary of the end surface T of the core wires S clearer.

As already described above, the storage device 9c of the computer 9 stores various data about the electric wire D, such as the model name of the electric wire D, the entire outer diameter of the plurality of core wires S taken as one piece of conductor (i.e., the conductor diameter), the outer diameter d of each of the core wires S (i.e., the core wire outer diameter d), and the number of the core wires S contained in the electric wire D (i.e., the number of core wires). In the following test, the core wire outer diameter d and the number of core wires are used.

At step S102, the CPU of the computer 9 searches for images of circular shapes contained in the binary coded image. The term "circular shape" herein refers to a circular shape such that it can be regarded as a core wire S. When cutting the electric wire D or stripping off the sheath H, the shape of the end surface of the core wires S may slightly deform at times. For this reason, the term "circular shape" herein is meant to include s lightly deformed circular shapes as well as the perfect circular shape. In other words, the term "circular shape" herein is meant to include the shapes that can be regarded as substantially circular shapes.

At step S103, it is determined whether or not a circular shape that matches a predetermined circular shape exists among the circular shapes that have been found. In other words, it is determined whether or not a circular shape having an outer diameter that matches the core wire outer diameter d stored in the storage device 9c exists among the circular shapes found at step S102. The criteria for the determination may be set as appropriate. In the present preferred embodiment, if the outer diameter of a circular shape falls within the range from about −10% to about +5%, for example, of the core wire outer diameter d, the circular shape is regarded as having an outer diameter that is substantially in agreement with the core wire outer diameter d, and the circular shape is regarded as being the predetermined circular shape. In other words, a circular shape having an outer diameter that falls within the range of from about −10% to about +5%, for example, of the core wire outer diameter d is regarded as being corresponding to one core wire. The outer diameter of a circular shape extracted from the binary-coded image and the core wire outer diameter d need not be compared by obtaining the difference therebetween, but may be compared by obtaining the ratio therebetween.

If the result of the determination at step S103 is YES, the matching circular shapes are counted at step S104. The circular shapes counted at step S104 are erased from the binary coded image data at step S105. Thereby, the circular shapes that have not yet been counted are left in the binary coded image data. Thereafter, the process returns to step S103, and the above-described steps are repeated. When executing the processes of the foregoing steps S103, S104, and S105, the computer 9 functions as the counting unit 9a.

When the computer 9 finishes counting all the circular shapes, the image data no longer contains any circular shape that matches the predetermined circular shape. Therefore, the result of the determination at step S103 becomes NO. If the result of the determination at step S103 is NO, it is determined at step S106 whether or not the count value matches the original number (the preset number) of core wires of the electric wire D. If the result of the determination is YES, it means that no core wire S is missing, and that the condition of the end portion of the electric wire D is so good that all the core wires S can be counted. Therefore, the process proceeds to step S107, wherein the electric wire D is determined to be a non-defective product. On the other hand, if the result of the determination is NO, it means that some of the core wires S are missing, or that the condition of the end portion of the electric wire D is so poor that some of the core wires S cannot be counted. Therefore, at step S108, the electric wire D is determined to be a defective product.

As described above, the testing apparatus A counts the number of the core wires S from the image of an end surface of the electric wire D that is photographed by the camera 3, and determines pass/fail of the electric wire D based on the number of the core wires S. With the testing apparatus A, it is less likely that, when some of the core wires S are missing, the testing apparatus A falsely determines a defective product as a non-detective product than with the testing apparatus that determines pass/fail of the electric wire D based on the total area of the end surfaces of the all the core wires S. Generally, when the core wires S are relatively untied, gaps are formed between the end surfaces T of the core wires S that are adjacent to each other, and portions of the gaps tend to be falsely determined as portions of the areas of the core wires S. However, the testing apparatus A does not make such a false determination because it determines pass/fail of the electric wire D based on the number of the core wires S. The testing apparatus A makes it possible to accurately test the condition of an end portion of the electric wire D from which the sheath H has been stripped off by the cutter unit 32.

When the core wires S are bent or untied, each of the core wires S is photographed smaller. The outer diameter of the core wire S extracted from the photographed image becomes smaller than the preset core wire outer diameter d. If the outer diameter of a circular shape extracted from the photographed image falls outside the permissible range, the circular shape is not counted as a core wire S, so it is regarded that the core wire S is missing. Therefore, it is possible to check not just the defective condition of missing ones of the core wires S but also other defective conditions such as bending and untying of the core wires S by a simple technique including counting the number of the core wires. Furthermore, with the testing apparatus A, an electric wire D containing a core wire S whose diameter has been altered for some reason can also be detected as a defective product.

Since the apparatus main unit 1 of the testing apparatus A preferably has a vertically elongated shape, the testing apparatus A can be incorporated in the electric wire processor B without occupying a large space therein. The testing apparatus A has a very simple overall configuration. Therefore, the testing apparatus A can be manufactured easily and at low cost.

The electric wire processor B is equipped with the testing apparatus A. Therefore, when the sheath H of the electric wire D has been stripped off in an undesirable way by the cutter unit 32, it is possible to detect the defective condition before the electric wire D is conveyed to the crimping unit. As a result, it becomes possible to eliminate defective products in advance. Crimping of a terminal onto a defective electric wire D can be prevented, so production of defective harnesses can be prevented in advance.

Second Preferred Embodiment

Figure 6:
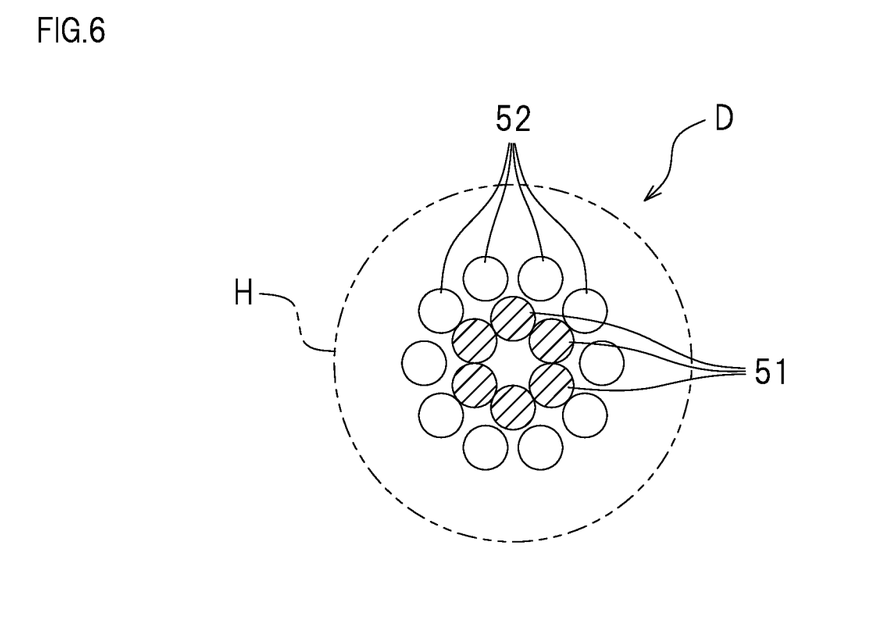
FIG. 6 is a view schematically illustrating an end surface of the core wires of an electric wire.
Figure 8:
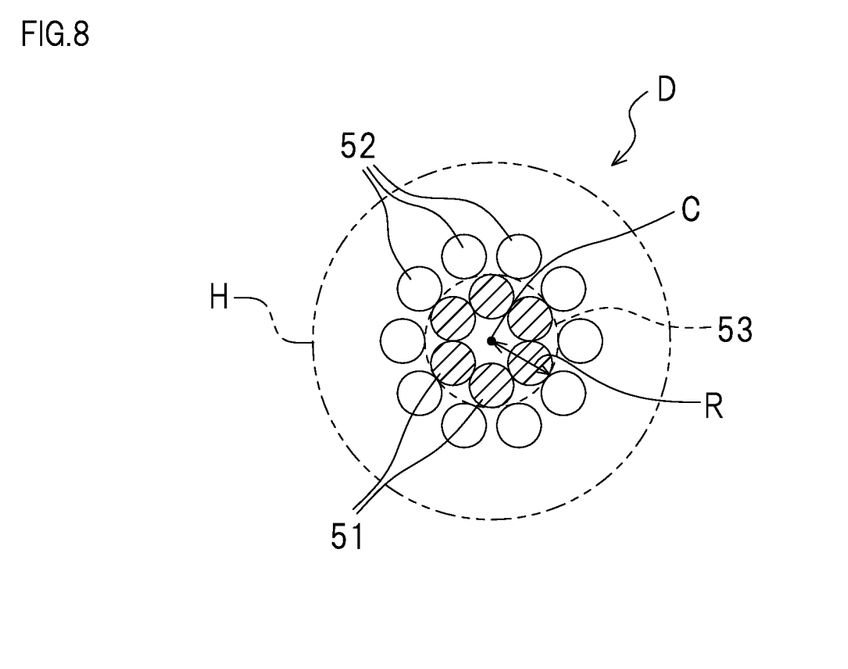
FIG. 8 is a view illustrating one example of a photographed image.

As illustrated in FIG. 6, an electric wire D including a plurality of inner core wires 51 and a plurality of outer core wires 52 disposed around the inner core wires 51 has been known. In FIGS. 6 and 8, the inner core wires 51 are indicated by hatching for convenience so that the inner core wires 51 and the outer core wires 52 can be easily distinguished from each other. Here, an electric wire D having six inner core wires 51 and 10 outer core wires 52 will be described as one example. It should be noted, however, that the numbers of the inner core wires 51 and the outer core wires 52 are not particularly limited. In addition, the electric wire that is the test subject of various preferred embodiments of the present invention may further have a plurality of other outer core wires disposed around the outer core wires 52.

As already described above, the electric wire D is cut by the cutter unit 32, and the sheath H is stripped off therefrom. When cutting the wire, the cutting blade 36 is pressed against the electric wire D, and a force is applied to the core wires S in a moving direction of the cutting blade 36 (i.e., in the direction orthogonal to the longitudinal direction of the core wires S). As a consequence, the core wires S are slightly compressed. Since the inner core wires 51 are surrounded by the outer core wires 52, the inner core wires 51 are compressed more easily than the outer core wires 52. When stripping off the sheath H, the stripping blades 37 cut into the sheath H from the outside of the sheath H. For this reason, the outer core wires 52 are more likely to be cut by the stripping blades 37 than the inner core wires 51. The inner core wires 51 are less likely to be damaged or lost than the outer core wires 52.

Because the inner core wires 51 are less likely to be damaged or lost than the outer core wires 52, pass/fail of the electric wire D can be determined based on only the number of the outer core wires 52 in the electric wire D having the inner core wires 51 and the outer core wires 52. The testing apparatus A according to the present preferred embodiment uses the electric wire D having the inner core wires 51 and the outer core wires 52, and it determines pass/fail of the electric wire D while regarding the entirety of the inner core wires 51 as one core wire. The configuration of the testing apparatus A is identical to that described in preferred embodiment 1, and is therefore not further elaborated upon. Hereinbelow, how the electric wire D is tested according to the present preferred embodiment will be described with reference to the flowchart of FIG. 7.

Figure 7:
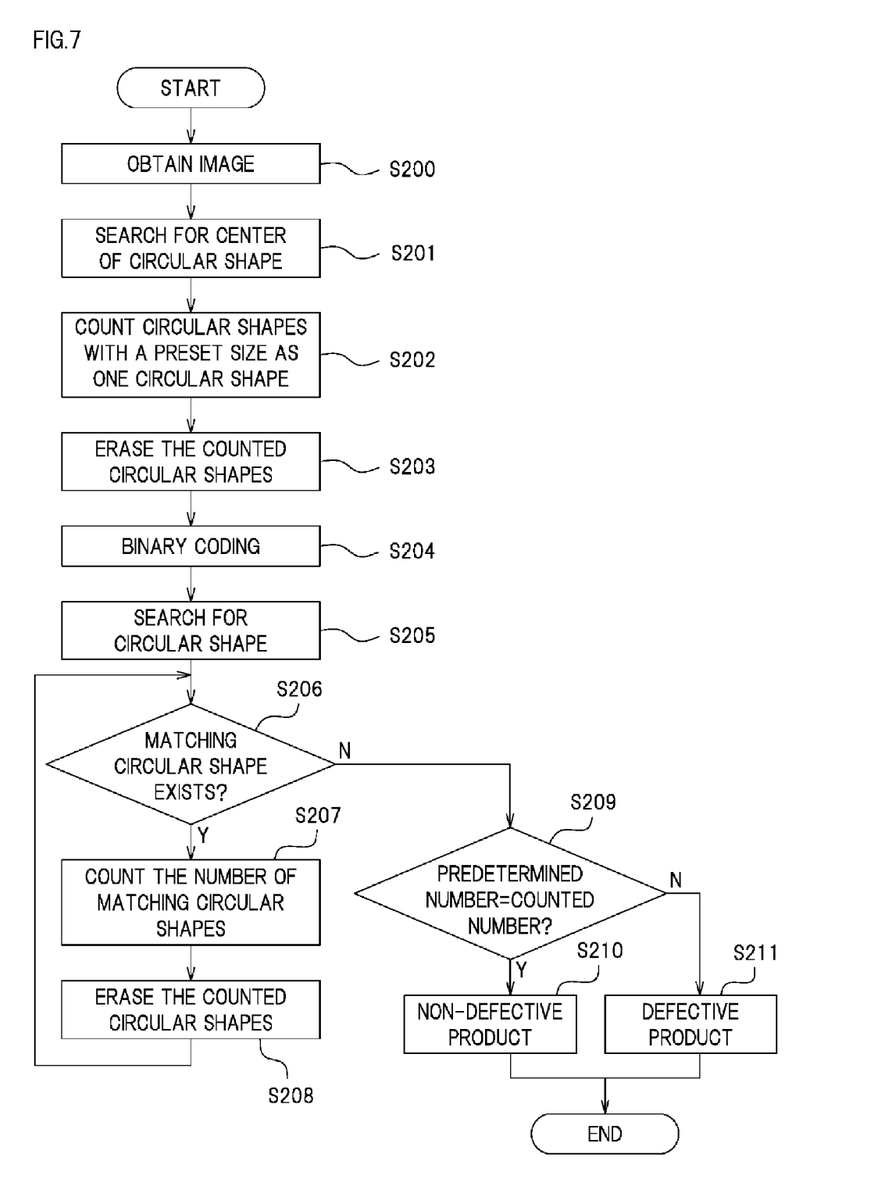
FIG. 7 is a flow-chart for illustrating a testing method according to a second preferred embodiment of the present invention.
Figure 9:
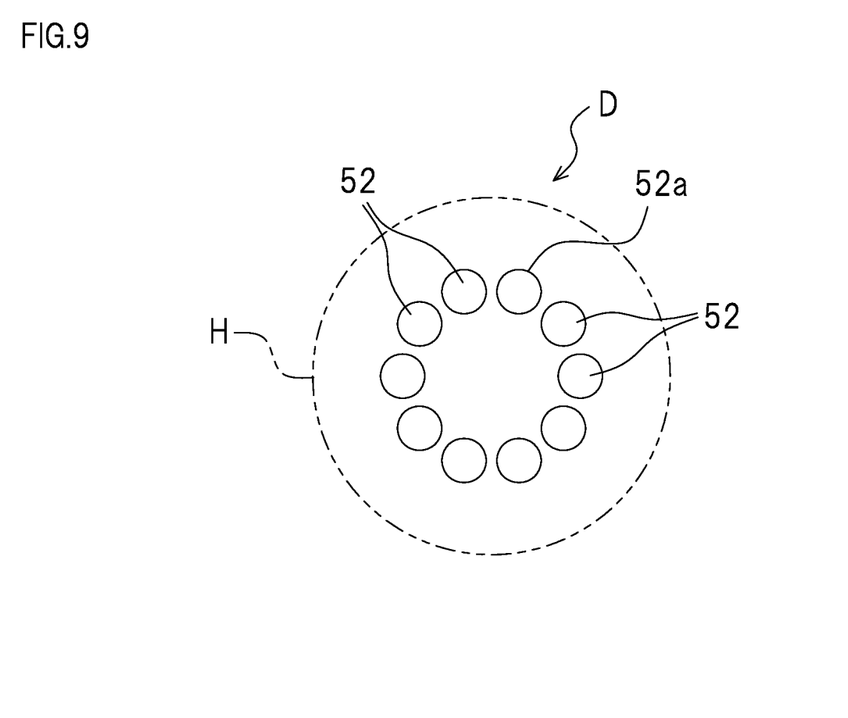
FIG. 9 is a view illustrating an image from which the circular shape corresponding to the inner core wires has been erased.

First, at step S200, data of the photographed image are taken into the computer 9. At step S201, the CPU of the computer 9 searches for the center C (see FIG. 8) of the entire end surface of the core wires of the electric wire D. In the electric wire D having the inner core wires 51 and the outer core wires 52, the inner core wires 51 are disposed evenly around the center C. At step S202, the CPU counts a circular shape 53 having a predetermined radius R and a center C as one core wire. In other words, the entirety of the inner core wires 51 is regarded as one core wire. Next, at step S203, the portion of the circular shape 53 is erased from the photographed image (see FIG. 9).

Figure 10:
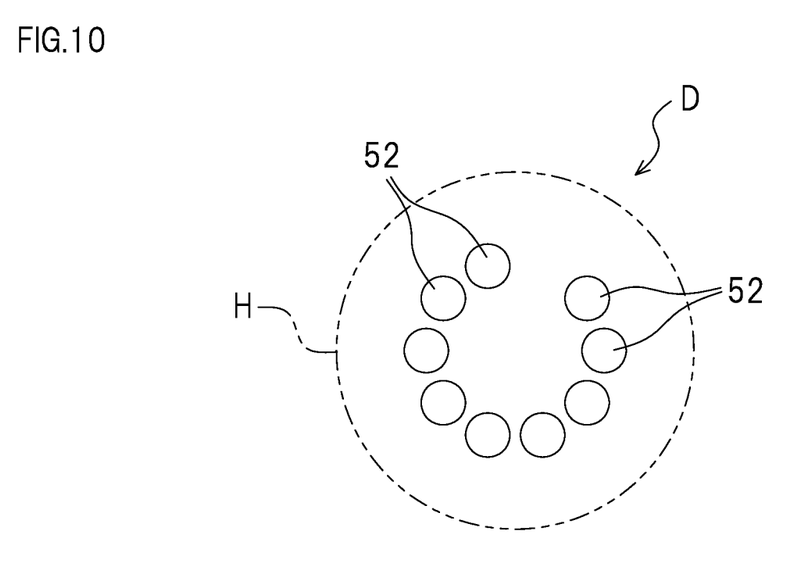
FIG. 10 is a view illustrating an image from which one of the circular shapes corresponding to the outer core wires has been erased.

Thereafter, the number of the outer core wires 52 is counted in the same manner as described in the first preferred embodiment. That is, at step S204, binary coding is performed based on a preset threshold value, for the image from which the circular shape 53 is erased. Next, at step S205, the CPU searches for images of the circular shapes contained in the binary coded image. At step S206, it is determined whether or not a circular shape that matches a predetermined circular shape exists among the circular shapes that have been found. If the result of the determination is YES, the matching circular shapes are counted at step S207, and the circular shapes are erased from the image at step S208. For example, in the image shown in FIG. 9, if it is determined that the top-right circular shape 52a matches the predetermined shape, the image from which the circular shape 52a has been erased results in the image as shown in FIG. 10. After step S208, the process returns to step S206, and the above-described steps are repeated.

When the computer 9 finishes counting all the circular shapes, the image no longer contains any circular shape that matches the predetermined circular shape. The result of the determination at step S206 becomes NO, and the process of step S209 is executed. At step S209, it is determined whether or not the count value matches the original number (the preset number) of core wires of the electric wire D. The preset number here means the number of core wires when the entirety of the inner core wires 51 of the electric wire D is regarded as one core wire. Since the electric wire D here has six inner core wires and 10 outer core wires, the just-mentioned preset number is 11.

If the result of the determination at step S209 is YES, it is determined at step S210 that the electric wire D is a nondefective product. On the other hand, if the result of the determination at step S209 is NO, it is determined at step S211 that the electric wire D is a defective product.

In the present preferred embodiment, the entirety of the inner core wires 51 is regarded as one core wire, and the number of the inner core wires 51 is not counted. Therefore, the test can be conducted in a simpler and quicker manner.

The inner core wires 51 are more likely to adhere to each other than the outer core wires 52 by the cutting with the cutter unit 32 and the stripping off of the sheath H. In addition, the cross-sectional shape of the inner core wires 51 is more apt to deform than that of the outer core wires 52. Moreover, the reflection of light tends to be stronger in a central portion of the electric wire D, so the image of the central portion tends to become unclear. For that reason, the boundary of the inner core wire 51 is more likely to be unclear than that of the outer core wire 52. The electric wire D having the inner core wires 51 and the outer core wires 52 has the feature that the number of the inner core wires 51 is more difficult to count accurately than that of the outer core wires 52. However, according to the present preferred embodiment, the number of the inner core wires 51 is not counted one by one. Therefore, the number of core wires can be counted more accurately. This makes it possible to test the end portion of the electric wire D having the inner core wires 51 and the outer core wires 52 more accurately.

In one type of electric wire D, a plurality of core wires are compressed to each other. The core wires of such an electric wire D is called "compressed conductor." In the electric wire D in which the inner core wires 51 and the outer core wires 52 are formed into a compressed conductor, the inner core wires 51 are very closely in contact with each other, so the boundaries of the inner core wires 51 tend to be more unclear. The testing apparatus A according to the present preferred embodiment is particularly useful for the electric wire D having a compressed conductor.

In the present preferred embodiment, the entirety of the inner core wires 51 is counted as one core wire. However, it is possible that pass/fail of the electric wire D may be determined based on the number of the outer core wires 52 alone, without counting the inner core wires 51. In this case, the preset number of the wires is 10, so it is determined at step S209 whether the count value is 10 or not.

Other Preferred Embodiments

It is not always necessary to incorporate the testing apparatus A according to the present invention in the electric wire processor B as shown in the foregoing preferred embodiments. The testing apparatus A may be incorporated in, for example, an apparatus for only stripping off the sheath H of the electric wire D. It is also possible to use the testing apparatus A alone.

The imaging device is not limited to the CCD camera 3 but may be other types of cameras, for example.

In the foregoing preferred embodiments, a single computer 9 is preferably used as both the counting unit and the determining unit. However, it is also possible that the counting unit and the determining unit may be constructed of separate computers, for example.

Although the conveying units 30 and 31 are configured to turn about the centers in the base end portions, it is not always necessary that the conveying units 30 and 31 are configured in this way. For example, the conveying units 30 and 31 may be configured to slide in horizontal directions. The conveying units 30 and 31 may convey the electric wire D in a direction perpendicular to their longitudinal direction.

In the foregoing preferred embodiments, the core wires S contained in the electric wire D preferably have the same outer diameter. However, the electric wire D may have a plurality of core wires S having different outer diameters.

In addition, the testing apparatus A and the electric wire processor B may be altered or modified freely as long as they are within the scope of the present invention.

Only selected preferred embodiments have been chosen to be described so as to illustrate the present invention. To those skilled in the art, however, it will be apparent from the foregoing disclosure that various changes and modifications can be made herein without departing from the scope of the present invention as defined in the appended claims. Furthermore, the foregoing description of the preferred embodiments according to the present invention is provided for illustration only, and not for limiting the present invention as defined by the appended claims and their equivalents.

What is claimed is:

1. An electric wire testing apparatus for testing a condition of an end portion of an electric wire including a plurality of core wires and a sheath covering the core wires, the electric wire testing apparatus comprising:
   an imaging device arranged to photograph an end surface of the core wires that have been exposed by stripping off the sheath;
   a counting unit arranged to count the number of the core wires based on an image photographed by the imaging device; and
   a determining unit arranged to determine pass/fail of the condition of the end portion of the electric wire based on whether or not the number of the core wires counted by the counting unit matches a predetermined number.

2. The electric wire testing apparatus according to claim 1, further comprising a storage device storing data about an outer diameter of the core wires, wherein the counting unit is configured to count the number of the core wires by extracting an outer diameter of an end surface of each of the core wires from the image photographed by the imaging device and comparing the extracted outer diameter with the outer diameter stored in the storage device.

3. The electric wire testing apparatus according to claim 1, wherein:
   the core wires include a plurality of inner core wires, and a plurality of outer core wires disposed around the inner core wires;
   the counting unit is configured to count a number of the outer core wires; and
   the determining unit is configured to determine pass/fail of the condition of the end portion of the electric wire based on the number of the outer core wires counted by the counting unit.

4. The electric wire testing apparatus according to claim 3, further comprising a storage device storing at least data about an outer diameter of the outer core wire, wherein the counting unit is configured to count the number of the outer core wires by extracting an outer diameter of an end surface of each of the outer core wires from the image photographed by the imaging device and comparing the extracted outer diameter with the outer diameter of the outer core wires stored in the storage device.

5. The electric wire testing apparatus according to claim 3, wherein the counting unit is configured to count all of the plurality of inner core wires as one core wire.

6. The electric wire testing apparatus according to claim 3, wherein the core wires are compressed to each other and define a compressed conductor.

7. An electric wire processor comprising:
   an electric wire testing apparatus according to claim 1;
   a conveying unit arranged to hold and convey the electric wire;
   a cutter unit arranged to cut the electric wire and strip off the sheath; and
   a terminal crimping unit arranged to crimp a terminal onto an end portion of the electric wire from which the sheath has been stripped off; wherein
   the electric wire testing apparatus is configured to test the condition of the end portion of the electric wire while the conveying unit is conveying the electric wire from the cutter unit to the terminal crimping unit.

* * * * *